United States Patent [19]

Bowden

[11] Patent Number: 5,750,769
[45] Date of Patent: May 12, 1998

[54] HALOGENATED ESTERS USEFUL AS INTERMEDIATES FOR INSECTICIDES

[75] Inventor: Martin Charles Bowden, Brighouse, United Kingdom

[73] Assignee: Zeneca Limited, London, England

[21] Appl. No.: 554,648

[22] Filed: Nov. 8, 1995

[30] Foreign Application Priority Data

Nov. 25, 1994 [GB] United Kingdom ............... 9423800
Jul. 18, 1995 [GB] United Kingdom ............... 9514652

[51] Int. Cl.$^6$ .................................................. C07C 69/66
[52] U.S. Cl. .................... 560/184; 560/177; 560/226; 562/577; 562/586; 562/603
[58] Field of Search ...................... 560/184; 562/586

[56] References Cited

U.S. PATENT DOCUMENTS 4,113,968  9/1978  Mori et al. .
4,183,948  1/1980  Huff ............................. 560/124
4,238,505  12/1980  Engel ........................... 560/124

FOREIGN PATENT DOCUMENTS 304271  2/1989  European Pat. Off. .
90/09995  9/1990  WIPO .
WO94/27942  12/1994  WIPO .

OTHER PUBLICATIONS

Search report in a corresponding British application.
Rydon, J. Chem. Soc. 1340 (1937).
Search Report in a corresponding international application.

*Primary Examiner*—Michael L. Shippen
*Attorney, Agent, or Firm*—Joel G. Ackerman

[57] ABSTRACT

The invention provides novel compounds of formula:

$$CF_3-CXCl-CH(OH)CH_2-C(CH_3)_2-CH_2-CO_2R \qquad (I)$$

where X represents chloro or bromo and R represents hydrogen or alkyl of up to 4 carbon atoms, processes for preparing them and their use as intermediates in the preparation of insecticidal cyclopropane derivatives. Also provided are novel compounds of formula:

$$BrCH_2-CH_2-C(CH_3)_2-CH_2-CO_2R \qquad (IV)$$

wherein R represents alkyl of up to 4 carbon atoms, useful as intermediates in the preparation of the compounds of formula I.

10 Claims, No Drawings

HALOGENATED ESTERS USEFUL AS INTERMEDIATES FOR INSECTICIDES

This invention relates to halogenated esters useful as intermediates for insecticides, to processes for preparing them and to processes for preparing insecticides from them.

UK Patent no 2000764 discloses valuable insecticidal esters, including α-cyano-3-phenoxybenzyl 3-(2-chloro-3,3,3-trifluoroprop-1-en-1-yl)-2,2-dimethylcyclopropane carboxylate, which in the form of the racemate formed by its (Z)-1R,cis-αS and (Z)-1S,cis-αR isomers is a widely used commercial insecticide having the ISO common name of lambda-cyhalothrin.

The present invention concerns novel halogenated esters which can be used as intermediates in the preparation of cis-3-(2-chloro-3,3,3-trifluoroprop-1-en-1-yl)-2,2-dimethylcyclopropane carboxylic acid (cyhalothrin acid) from which lambda-cyhalothrin is manufactured.

Accordingly the present invention provides a compound of formula:

$$CF_3—CXCl—CH(OH)CH_2—C(CH_3)_2—CH_2—CO_2R \quad (I)$$

where X represents chloro or bromo and R represents hydrogen or alkyl of up to 4 carbon atoms. Particular examples of compounds of formula I include methyl 6-bromo-6-chloro-3,3-dimethyl-5-hydroxy-7,7,7-trifluoroheptanoate, ethyl 6-bromo-6-chloro-3,3-dimethyl-5-hydroxy-7,7,7-trifluoroheptanoate, methyl 6,6-dichloro-3,3-dimethyl-5-hydroxy-7,7,7-trifluoroheptanoate, and ethyl 6,6-dichloro-3,3-dimethyl-5-hydroxy-7,7,7-trifluoroheptanoate, and the corresponding carboxylic acids.

The present invention also provides a process for preparing a compound of formula I where X represents chloro or bromo and R represents alkyl of up to 4 carbon atoms, which comprises reacting a compound of formula:

$$CF_3—CHXCl \quad (II)$$

with a compound of formula:

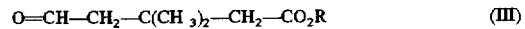

$$O=CH—CH_2—C(CH_3)_2—CH_2—CO_2R \quad (III)$$

in the presence of a strong base and an inert solvent.

The process is conducted in the presence of a strong base, which is believed to act by generating a perhaloalkyl ion which then reacts with the aldehyde. Suitable strong bases include alkali metal lower alkoxides, such as sodium or potassium alkoxides containing up to 6 carbon atoms, for example sodium isopropoxide, potassium isopropoxide, sodium t-butoxide or potassium t-butoxide, but other bases such as alkali metal hydrides, for example sodium hydride, and alkali metal amides, for example sodamide, may also be used. The process is preferably conducted at lower temperatures to avoid the production of unwanted by-products. A preferred temperature is within the range –80° C. to 0° C., especially where a polar aprotic solvent is used. Particular examples of polar aprotic solvents which may be useful in the process include amides such as dimethylformamide, dimethylacetamide and di-n-butylacetamide, cyclic ethers such as tetrahydrofuran, tetrahydropyran and dioxan, glycol ethers such as ethylene glycol dimethyl ether, and ethylene glycol diethyl ether, and sulphoxides such as dimethyl sulphoxide. However other inert solvents such as aromatic hydrocarbons e.g. toluene may also be used.

The compounds of formula III may be obtained by reacting a compound of formula:

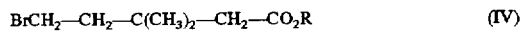

$$BrCH_2—CH_2—C(CH_3)_2—CH_2—CO_2R \quad (IV)$$

with an oxygen donor and a base. Pyridine N-oxide is a suitable oxygen donor, and the base is conveniently an alkali metal carbonate, such as sodium or potassium carbonate.

The compounds of formula IV are believed not to have been previously described and accordingly in a further aspect of the present invention there is provided a compound of formula IV wherein R is alkyl of up to 4 carbon atoms, preferably methyl and ethyl.

The compounds of formula IV may be obtained by reacting a compound of formula:

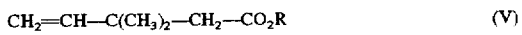

$$CH_2=CH—C(CH_3)_2—CH_2—CO_2R \quad (V)$$

with hydrogen bromide in the presence of a free-radical catalyst, such as an organic peroxide.

The compounds of formula I may be converted into cyhalothrin acid (as its alkyl ester) by a simple two step process. Accordingly in a yet further aspect of the present invention there is provided a process for preparing an alkyl ester of 3-(2-chloro-3,3,3-trifluoroprop-1-en-yl)-2,2-dimethylcyclopropane carboxylic acid which comprises the a) treating the compound of formula I with a dehydration agent to obtain a compound of formula:

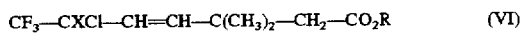

$$CF_3—CXCl—CH=CH—C(CH_3)_2—CH_2—CO_2R \quad (VI)$$

and (b) treating the compound of formula VI with at least one molar equivalent of a base in an inert solvent, and recovering the alkyl ester of 3-(2-chloro-3,3,3-trifluoroprop-1-en-yl)-2,2-dimethylcyclopropane carboxylic acid from the reaction mixture.

A preferred dehydration agent for use in step (a) is phosphorus oxychloride, and the process is preferably conducted in a suitable solvent such as a pyridine base, for example lutidine. The base used in step (b) is preferably a alkali metal alkoxide, and the process may be carried out in a suitable solvent or diluent such as for example a polar aprotic solvent such as dimethylformamide or an excess of the alcohol corresponding to the alkali metal alkoxide. Sodium or potassium t-butoxide are preferred bases and the reaction is preferably carried out in dimethylformamide. Other bases such as alkali metal amides, eg sodamide, or alkali metal disilylazides, eg sodium disilylazide, may also be used, preferably in the presence of a catalytic quantity of an alkanol such as t-butanol. A particularly useful technique for use in step (b) is to carry out the reaction in the presence of an aromatic hydrocarbon solvent such a toluene or xylene under conditions that remove the t-butanol by distillation.

Further details of the processes involved in preparing and using the compounds of formula I are set forth in the following Examples which are illustrative of the various aspects of the invention.

EXAMPLE 1

This Example illustrates the preparation of methyl 5-bromo-3,3-pent-4-enoate.

Methyl 3,3-dimethyl pentenoate (50.0 g) was dissolved in carbon tetrachloride (500 cm³) and warmed to 60° C. under a nitrogen atmosphere. Benzoyl peroxide (2.44 g) was added in one portion and the mixture stirred for 10 minutes, after which a stream of gaseous hydrogen bromide was introduced through a glass sinter over a period of 45 minutes. The reaction mixture was purged with nitrogen and maintained at the ambient temperature for 72 hours. The mixture was then warmed to 50° C., a further quantity (2.44 g) of benzoyl peroxide added, and gaseous hydrogen bromide introduced over a period of 15 minutes to complete the reaction. After removal of residual hydogen bromide by sparging with nitrogen the reaction mixture was concentrated by removal of the solvent by evaporation under reduced pressure. The residual liquid was purified by distillation to obtain methyl 5-bromo-3,3-dimethylpentanoate as a colourless liquid, b.p. 80° C./2 mm Hg, yield 80%).

H$^1$ NMR (ppm): 3.70 (3H,s,OMe); 3.40 (2H,m,CH$_2$Br); 2.25 (2H,s,CH$_2$CO$_2$Me); 1.95 (2H,m,CH$_2$); 1.05 (6H,s, CMe$_2$)

EXAMPLE 2

This Example illustrates the preparation of methyl 3,3-dimethyl-5-oxopentanoate.

A mixture of methyl 5-bromo-3,3-dimethylpentanoate (5.0 g), pyridine-N-oxide (4.49 g), sodium bicarbonate (3.77 g) and toluene (30 cm$^3$) was heated at the reflux temperature with vigorous agitation for a period of 14 hours. After cooling the mixture to the ambient temperature, water (20 cm$^3$), saturated ammonium carbonate solution (20 cm$^3$) and toluene (50 cm$^3$) were added and the aqueous phase separated and extracted with toluene (3×75 cm$^3$). The toluene extracts were added to the main organic phase and the whole dried over anhydrous magnesium sulphate concentrated by evaporation of the more volatile components under reduced pressure. The residual liquid was purified by Kugelrohr distillation (130° C./water pump pressure) to give methyl 3,3-dimethyl-5-oxopentanoate in 63% yield.

H$^1$ NMR (ppm): 9.85 (1H,m,CHO); 3.65 (3H,s,OMe); 2.50 (2H,m,CH$_2$CHO); 2.40 (2H,s,CH$_2$CO$_2$Me); 1.15 (6H, s,CMe$_2$)

EXAMPLE 3

This Example illustrates the preparation of methyl 6,6-dichloro-3,3-dimethyl-5-hydroxy-7,7,7-trifluoroheptanoate.

To an agitated mixture of methyl 3,3-dimethyl-5-oxopentanoate (1.0 g), 1,1-dichloro-2,2,2-trifluoroethane (1.06 g) and dry tetrahydrofuran (10 cm$^3$), maintained at −78° C., was added, over a period of 5 minutes, sodium t-butoxide (1.66 cm$^3$ of a 42% w/w solution in dimethylformamide) after which the mixture continued to be agitated at −78° C. for a further 60 minutes. The reaction was quenched with saturated ammonium chloride at low temperature and the mixture allowed to warm to the ambient temperature. After addition of water (20 cm$^3$) and separation of the organic phase, the aqueous phase was extracted with di-isopropyl ether (3×30 cm$^3$) and the extracts combined with the organic phase, which was washed with brine (2×10 cm$^3$) and dried over anhydrous magnesium sulphate. After removal of the volatile components by evaporation under reduced pressure the residual oil was purified by column chromatography (silica gel column eluted with a 9:1 mixture (by volume) of hexane and ethyl acetate) to give methyl 6,6-dichloro-3,3-dimethyl-5-hydroxy-7,7,7-trifluoroheptanoate as a colourless oil (yield 56%).

H$^1$ NMR (ppm): 4.50 (1H,d,OH); 4.28 (1H,m,CHOH); 3.73 (3H,s,OMe); 2.48 (2H,d[ab],CH$_2$CO$_2$Me); 1.95 (2H, m,CH3); 1.15 (3H,s,CMe$_2$); 1.09(s,3H,CMe$_2$).

MS: 279 (M—OMe); 257 (M—[Cl+H$_2$O)].

Infra Red : 1710, 3400 cm$^{-1}$ (br)

EXAMPLE 4

This Example illustrates the preparation of methyl 6,6-dichloro-3,3-dimethyl-7,7,7-trifluorohept-4-enoate.

Phosphorus oxychloride (10 cm$^3$) was added dropwise to a stirred solution of methyl 6,6-dichloro-3,3-dimethyl-5-hydroxy-7,7,7-trifluoroheptanoate (5.49 g) in 3,5-lutidine (50 cm$^3$) maintained at 0° C. The resultant mixture was heated at 100° C. for 30 minutes, and then cooled to the ambient temperature under a nitrogen atmosphere, and poured into a stirred mixture of ice and water (300 cm$^3$). The mixture was extracted with ethyl acetate (2×150 cm$^3$), diethyl ether (3×150 cm$^3$) and finally with ethyl acetate (150 cm$^3$). The volume of the combined extracts was reduced to about 400 cm$^3$ by evaporation of some of the solvents under reduced pressure, and then washed with dilute (3.5M) hydrochloric acid. The aqueous washings were extracted with diethyl ether (3×50 cm$^3$) and the extracts combined with the organic phase. After washing the combined organic phase with brine and drying over anhydrous magnesium sulphate, the solvents were removed by evapoation under reduced pressure and the residual oil purified by Kugelrohr distillation (128° C./1 mm Hg) to give methyl 6,6-dichloro-3,3-dimethyl-7,7,7-trifluorohept-4-enoate as a pale yellow oil (2.86 g, 52% yield), together with a quantity of the allylically rearranged isomer methyl 4,6-dichloro-3,3-dimethyl-7,7,7-trifluorohept-5-enoate.

H$^1$ NMR (ppm): 6.50 (1H,d,=CH); 5.70 (1H,d,=CH); 3.65 (3H,s,OMe); 2.40 (2H,s,CH$_2$CO$_2$Me); 1.25 (6H,s, CMe$_2$).

MS: 257 (M—Cl), 219 (M—CH$_2$CO$_2$Me).

Infra red : 1750 cm$^{-1}$.

EXAMPLE 5

This Example illustrates the preparation of ethyl 3-(2-chloro-3,3,3-trifluoroprop-1-en-1-yl)-2,2-dimethylcyclopropane carboxylate.

A stirred solution of ethyl 6,6-dichloro-3,3-dimethyl-7,7,7-trichlorohept-4-enoate (0.1 g) in dimethylformamide (10 ml) was cooled to −25° C. under a nitrogen atmosphere and sodium t-butoxide (0.1 ml of a 42% solution in dimethylformamide) added dropwise. After 30 minutes five further drops of the sodium t-butoxide solution was added and the mixture stirred for a further 15 minutes, before the reaction was quenched with saturated ammonium chloride solution (2 ml) over a 10 minutes period. Water (40 ml) was added and the mixture extracted with hexane (3×40 ml) the combined extracts washed with brine (20 ml) and dried over anhydrous sodium sulphate. The dried solution was filtered and concentrated by evaporation under reduced pressure to give ethyl 3-(2-chloro-3,3,3-trifluoroprop-1-en -1-yl)-2,2-dimethylcyclopropane carboxylate as a mixture of isomers.

EXAMPLE 6

This Example illustrates the preparation of methyl 3-(2-chloro-3,3,3-trifluoroprop-1-en-1-yl)-2,2-dimethylcyclopropane carboxylate.

By the use of a procedure similar to that described in the previous example the desired product was obtained by treating a solution of methyl 6,6-dichloro-3,3-dimethyl-7,7, 7-trifluorohept-4-enoate (0.217 g) in dry dimethylformamide (10 ml) at 0° C. under a nitrogen atmosphere with sodium t-butoxide (0.2 ml of a 42% solution in dimethylformamide). The identity of the product was confirmed by gas chromatographic mass spectroscopy as consisting principally of methyl cis-3-(Z-2-chloro-3,3,3-trifluoroprop-1-en-1-yl)-2,2-dimethyl cyclopropane carboxylate.

EXAMPLE 7

This Example illustrates the preparation of methyl 3-(2-chloro-3,3,3-trifluoroprop-1-en-2-yl)-2,2- dimethylcyclopropane carboxylate under conditions where the t-butanol is removed by azeotropic distillation with toluene.

Sodium t-butoxide (2.5 g) was added quickly to a mixture of methyl 6,6-dichloro-3,3-dimethyl-7,7,7-trifluorohept-4-enoate (5.55 g, strength 91%) and toluene (50 cm³) maintained under atmospheric pressure at 40° C. The resultant mixture was agitated as the pressure was reduced to 40 mm Hg and maintained at that value for 2 hours, after which the pressure was restored to atmospheric and the mixture quenched with acetic acid (4.0 cm³). Sampling of the mixture by quantitative gas chromatographic analysis demonstrated that the desired product (as cis-Z isomers) was present in a yield of 75%.

EXAMPLE 8

This Example illustrates the preparation of methyl 3-(2-chloro-3,3,3-trifluoroprop-1-en-2-yl)-2,2-dimethylcyclopropane carboxylate under conditions where the t-butanol is removed by azeotropic distillation with xylene.

The procedure of the previous Example was used except that xylene (50 cm³) was employed in place of toluene and the reduced pressure was 20 mm Hg, and was maintained for 2.5 hours. During this period additional xylene was added to maintain a constant volume. Sampling of the reaction mixture demonstrated the desired product (as cis-Z isomers) was obtained in a yield of 75%.

I claim:

1. A compound of formula:

$$CF_3-CXCl-CH(OH)CH_2-C(CH_3)_2-CH_2-CO_2R \qquad (I)$$

where X represents chloro or bromo and R represents hydrogen or alkyl of up to 4 carbon atoms.

2. A compound according to claim 1 wherein X represents chloro and R represents methyl.

3. A process for preparing a compound having the formula $CF_3-CXCl-CH(OH)Cl_2-C(CH_3)_2-CH_2-CO_2R$ where X represents chloro or bromo and R represents alkyl of up to 4 carbon atoms, which comprises reacting a compound of formula:

$$CF_3-CHXCl \qquad (II)$$

with a compound of formula:

$$O=CH-CH_2-C(CH_3)_2-CH_2-CO_2R \qquad (III)$$

in the presence of a strong base and an inert solvent.

4. The process according to claim 3 wherein the strong base is an alkali metal alkoxide.

5. The process according to claim 4 wherein the alkali metal alkoxide is sodium or potassium t-butoxide.

6. The process according to claim 3 conducted within the temperature range of −80° to 0° C.

7. The process according to claim 3 wherein the compound of formula III is obtained by the additional step of reacting a compound of formula:

$$BrCH_2-CH_2-C(CH_3)_2-CH_2-CO_2R \qquad (IV)$$

with pyridine N-oxide and a base.

8. The process according to claim 7 wherein the base is an alkali metal carbonate.

9. The process according to claim 7 wherein the compound of formula IV is obtained by the additional step of reacting a compound of formula:

$$CH_2=CH-C(CH_3)_2-CH_2-CO_2R \qquad (V)$$

with hydrogen bromide in the presence of a free-radical catalyst.

10. The process according to claim 9 wherein the free-radical catalyst is an organic peroxide.

* * * * *